United States Patent [19]

Trimble et al.

[11] Patent Number: 4,782,832

[45] Date of Patent: Nov. 8, 1988

[54] NASAL PUFF WITH ADJUSTABLE SEALING MEANS

[75] Inventors: Russell L. Trimble, Overland Park, Kans.; Roger J. Dolida, Kingwood, Tex.; Frederick R. Rose; Philip M. Metzler, both of Overland Park, Kans.

[73] Assignee: Puritan-Bennett Corporation, Lenexa, Kans.

[21] Appl. No.: 79,881

[22] Filed: Jul. 30, 1987

[51] Int. Cl.$^4$ .......................................... A61M 15/08
[52] U.S. Cl. .............................................. 128/207.18
[58] Field of Search ....................... 128/207.18, 204.18, 128/207.13

[56] References Cited

U.S. PATENT DOCUMENTS

| | | |
|---|---|---|
| 7,476 | 7/1850 | Lane . |
| 855,439 | 5/1907 | Clark .............................. 128/207.18 |
| 1,109,318 | 9/1914 | Browne et al. . |
| 1,162,416 | 11/1915 | Teter . |
| 1,632,449 | 6/1927 | McKesson . |
| 2,016,212 | 5/1934 | O'Connell . |
| 2,122,897 | 7/1938 | Straw . |
| 2,185,997 | 1/1940 | Heidbrink ...................... 128/207.18 |
| 2,241,535 | 5/1941 | Boothby et al. . |
| 2,245,969 | 6/1941 | Francisco ...................... 128/207.18 |
| 2,259,817 | 10/1941 | Hawkins ........................ 128/207.18 |
| 2,300,273 | 10/1942 | Conneil . |
| 2,376,971 | 5/1945 | Kleit . |
| 2,408,136 | 9/1946 | Fox . |
| 3,357,428 | 12/1967 | Carlson . |
| 3,362,404 | 1/1968 | Beasley . |
| 3,508,543 | 4/1970 | Aulicono ................... 128/207.18 X |
| 3,584,621 | 6/1971 | Bird et al. . |
| 3,799,164 | 3/1974 | Rollins . |
| 3,889,671 | 6/1975 | Baker . |
| 4,077,404 | 3/1978 | Elam . |
| 4,151,843 | 5/1979 | Brekke et al. . |
| 4,210,174 | 7/1980 | Eross . |
| 4,249,527 | 2/1981 | Ko et al. . |
| 4,266,540 | 5/1981 | Panzik . |
| 4,334,533 | 6/1982 | Henkin . |
| 4,354,488 | 10/1982 | Bartos . |
| 4,367,735 | 1/1983 | Dali .............................. 128/207.18 |

FOREIGN PATENT DOCUMENTS

| | | |
|---|---|---|
| 223220 | 2/1909 | Fed. Rep. of Germany . |
| WO82/03548 | 10/1982 | PCT Int'l Appl. . |
| WO84/02080 | 6/1984 | PCT Int'l Appl. . |
| WO86/06638 | 11/1986 | PCT Int'l Appl. . |
| 551609 | 3/1943 | United Kingdom . |
| 684788 | 12/1952 | United Kingdom . |
| 888546 | 1/1962 | United Kingdom . |
| 2147506A | 5/1985 | United Kingdom . |

OTHER PUBLICATIONS

Martin, R. J. et al., "Acute and Long-Term Ventilatory Effects of Hyperoxia in the Adult Sleep Apnea Syndrome", *Am. Rev. Respir. Dis.* 1982; 125:175–180.

Rapaport, D. M. et al., "Reversal of the 'Pickwickian Syndrome' by Long-Term Use of Nocturnal Nasa-1-Airway Pressure", *The New England Journal of Medicine, Medical Intelligence*, vol. 307, No. 15, Oct. 7, 1982, pp. 931–933.

Case Reports—"Remission of Severe Obesity-Hypoventilation Syndrome after Short-Term Treatment During Sleep with Nasal Continuous Positive Airway Pressure", *Am. Rev. Respir. Dis.* 1983:128:177–181.

Sullivan, C. E. et al., "Reversal of Obstructive Sleep Apnea by Continuous Positive Airway Pressure Applied Through the Nares", *The Lancet*, pp. 862–865, Apr. 18, 1981.

*Primary Examiner*—Alan Cohan
*Attorney, Agent, or Firm*—Hovey, Williams, Timmons & Collins

[57] ABSTRACT

An improved nasal puff assembly is provided which is of particular benefit in the treatment of obstructive sleep apnea and which is characterized by a gas-delivery puff which fits only in the nose of the patient and is therefore of relatively small size and can be comfortably worn. The nasal puff of the invention advantageously includes a plenum chamber having an inlet and a pair of laterally spaced outlets; a pair of soft synthetic resin nares elements or pillows are operatively coupled with the spaced plenum outlets and are designed for ready adjustability so that the effective positions thereof can be altered individually for permitting custom fitting of the nares elements with respect to the nares of different patients. In this way a relatively small number of different sizes of nasal puff can be modified to meet the needs of virtually all patients.

12 Claims, 4 Drawing Sheets

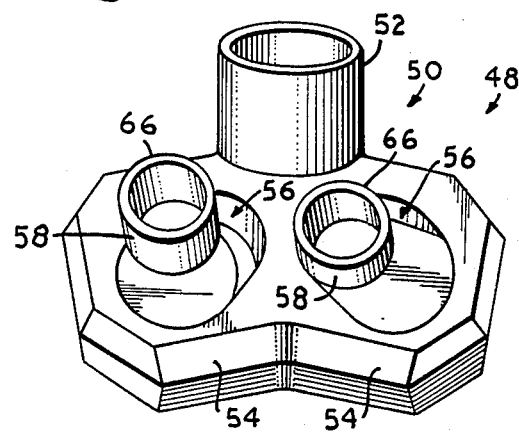
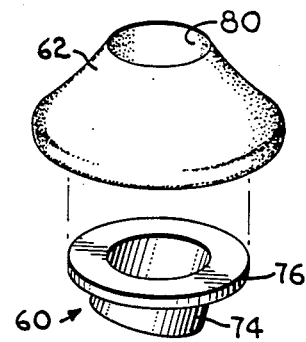
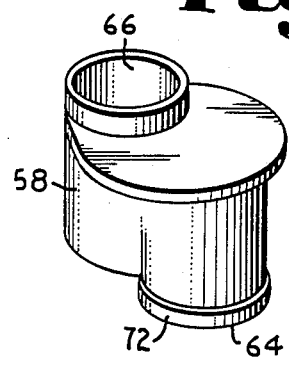
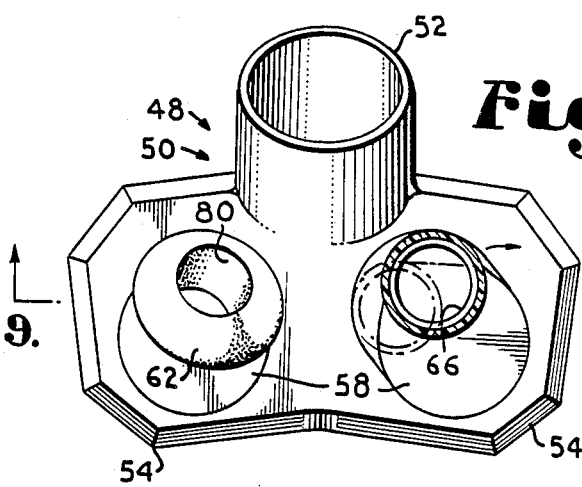
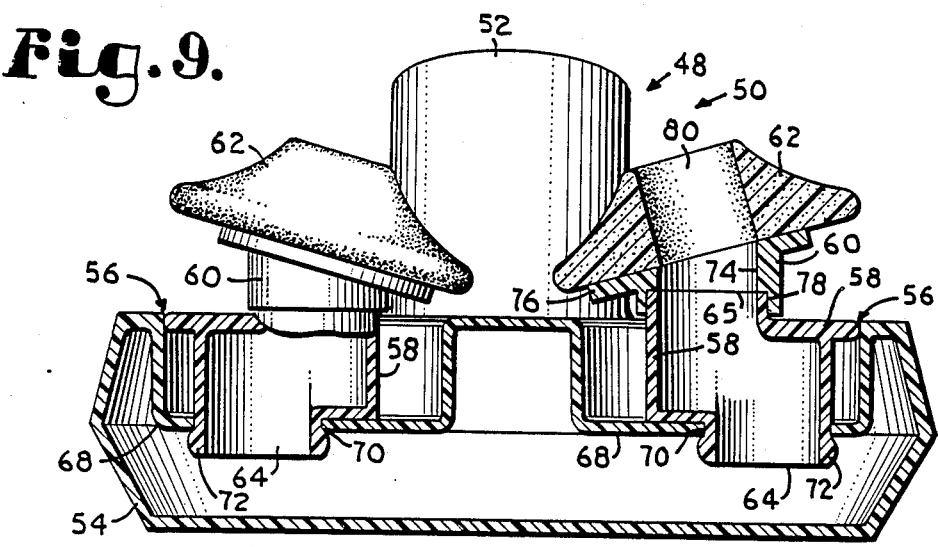

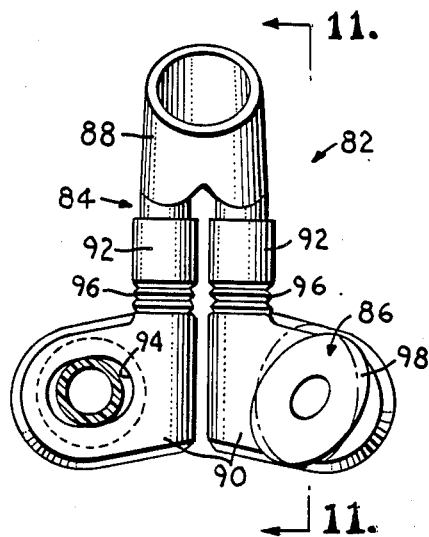
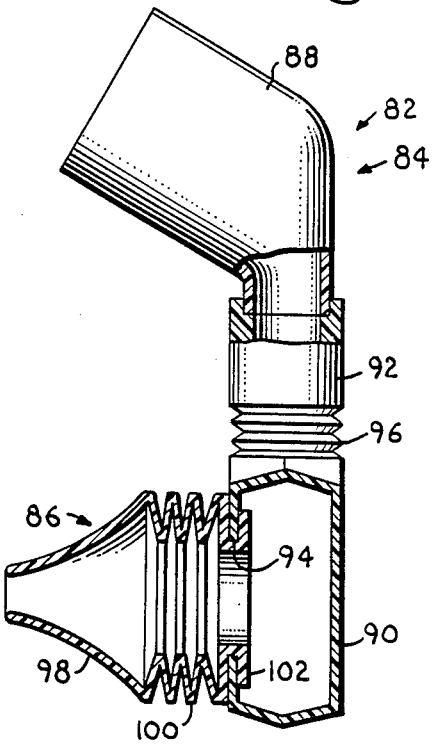
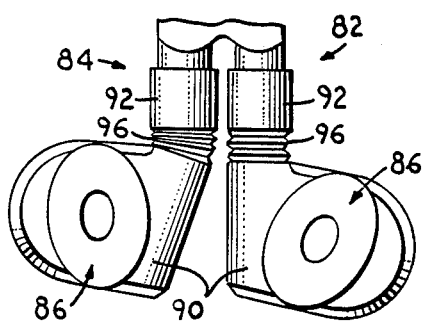
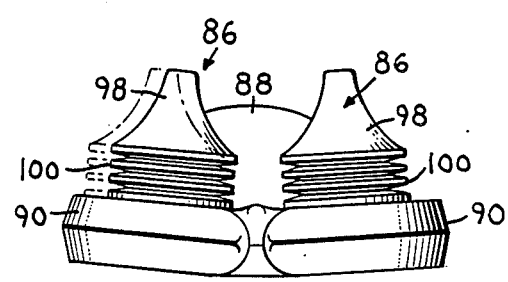
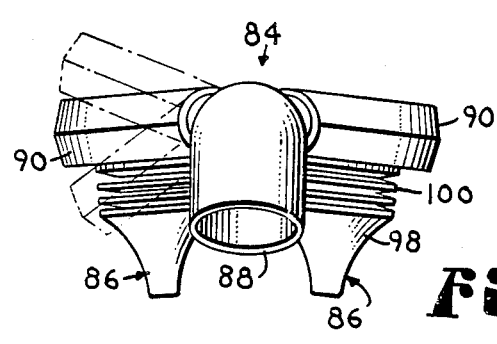

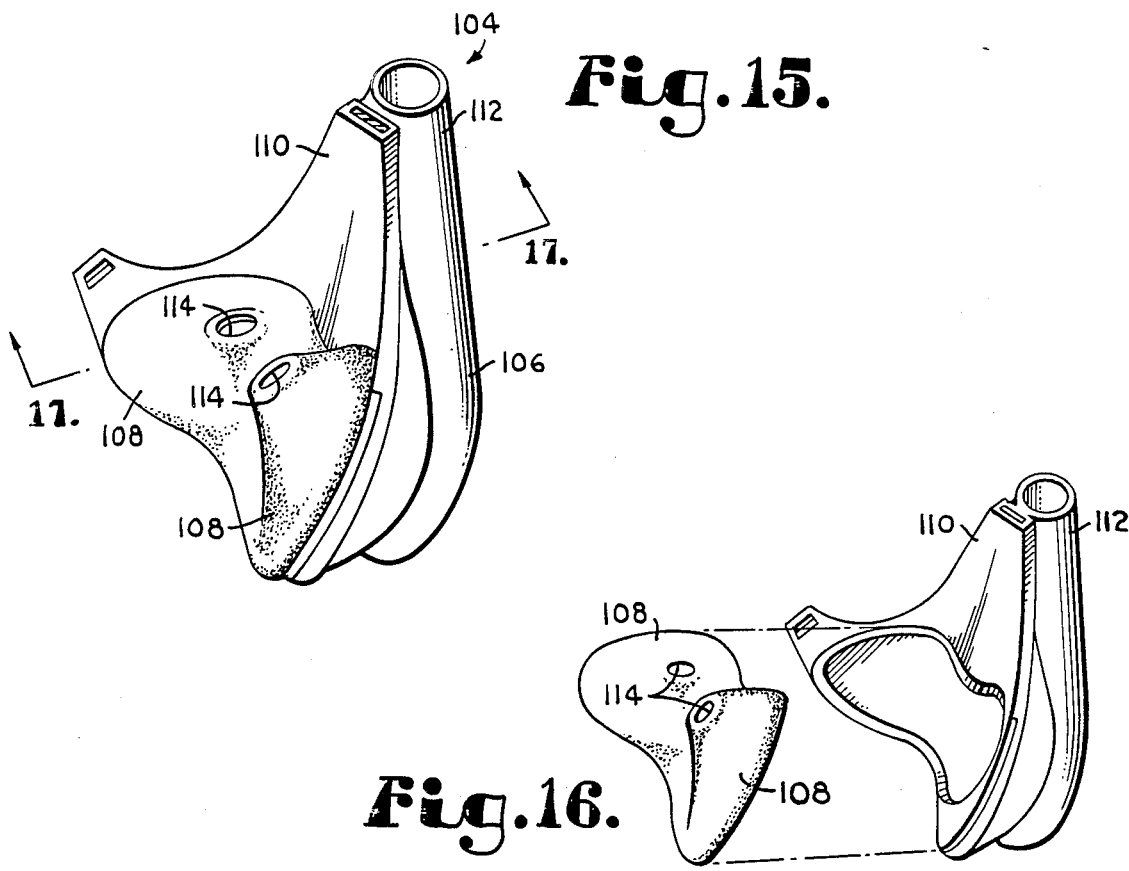
Fig. 15.
Fig. 16.
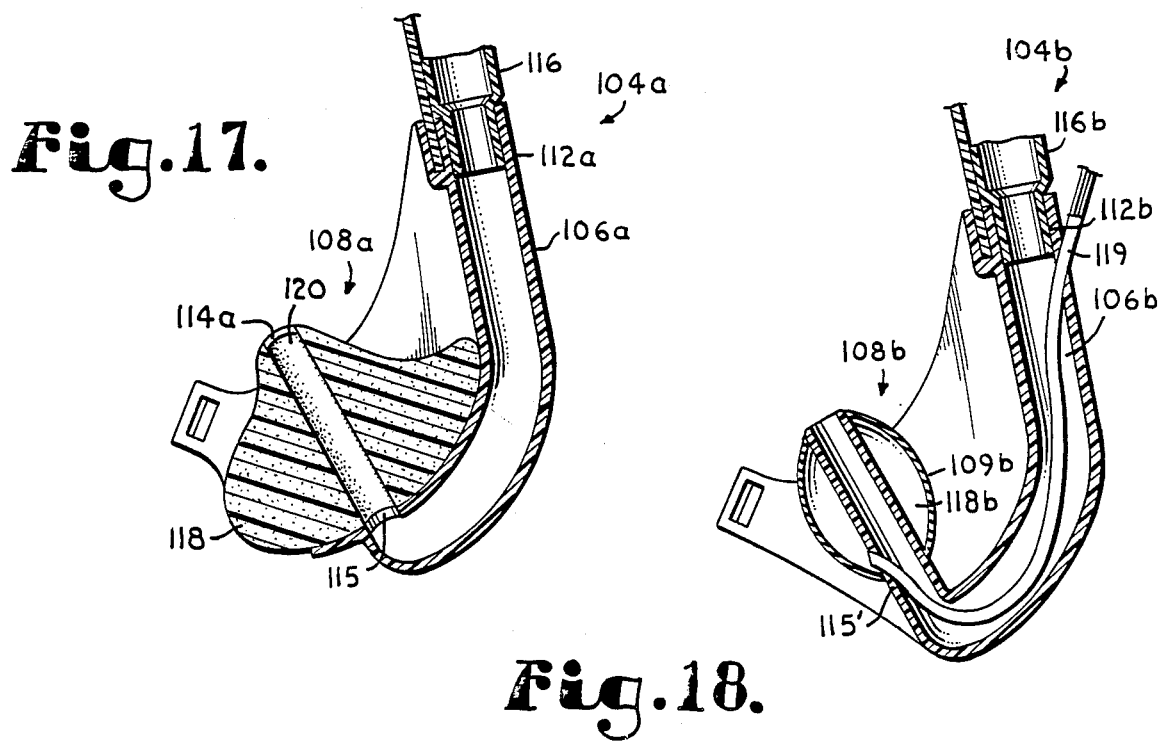
Fig. 17.
Fig. 18.

NASAL PUFF WITH ADJUSTABLE SEALING MEANS

BACKGROUND OF THE INVENTION

1. Field of the Invention

The present invention is broadly concerned with nasal puff devices particularly designed to be comfortable for the wearer and to thereby facilitate treatment of breathing disorders such as sleep apnea, ventilation difficulties or anesthetic gas administration (e.g., nitrous oxide). More particularly, it is concerned with such a nasal puff device which preferably includes a plenum chamber adapted to be coupled to a source of gas such as oxygen or air, together with a pair of gas delivery elements coupled with the plenum chamber and configured for insertion into the nares of a patient; very advantageously, the nares elements include means for selective alteration of the effective position thereof individually, for permitting custom fitting of the elements with respect to the nares of different patients.

2. Description of the Prior Art

In recent years, the condition of obstructive sleep apnea has been recognized as a serious one requiring therapeutic intervention. Those suffering from obstructive sleep apnea (most commonly obese males or obese females after menopause) may experience as many as six hundred apneaic events per night, each of which may last on the order of ten seconds or more. In each of these occurrences, there is essentially no air movement for a significant period and the patient is technically suffocating. As a consequence, the oxygen level in the blood drops, thereby inducing a high level of consciousness in the sufferer who then rouses and begins to breathe normally again. However, repeated occurrences of these apneaic events causes a definite lack of restful sleep and, by virtue of depleted oxygen levels in the blood, can lead to heart problems as well.

It has been proposed in the past to treat sleep apnea by means of continuous positive airway pressure (CPAP). This system involves applying a constant gas pressure, typically with air, through the nasal passages of the patient, so as to prevent negative pressure conditions within the thorax and to allow air to continuous flow through the upper air passageways. CPAP therapy has been in use for the last several years, and it is estimated that approximately five thousand patients are now being treated using this technique. Generally speaking, CPAP treatment involves placing a mask over the nose of the patient by means of a harness or other form of headgear, and coupling the mask to a source of positive, low pressure air. However, conventional masks used in this context are relatively cumbersome and noisy due to air leaks. Indeed, the problems associated with wearing a conventional mask during periods of attempted sleep are so formidable that many patients forego the therapy for this reason alone.

There is therefore a decided need in the art for a respiratory-assist device which can be comfortably worn by a patient during relatively long periods of rest and sleep, without the attendant problems of noise, discomfort or improper fit. Such a device would be useful not only in connection with sleep apnea therapy, but also in other types of respiratory therapy as well.

SUMMARY OF THE INVENTION

The present invention overcomes the problems described above, and provides a greatly improved respiratory therapy device in the form of a nasal puff of relatively small size adapted to be worn adjacent the nose of a wearer-patient. The nasal device advantageously includes a relatively small plenum chamber including structure defining an inlet adapted for coupling with a source of gas, and a pair of spaced apart, separate gas outlets in communication with the inlet. Typically, the plenum chamber is advantageously in the form of a generally Y-shaped in plan hollow body, with the gas outlets being located in the branches of the body. In any event, the preferred nasal puff of the invention further includes a pair of gas delivery elements each having a gas flow passageway therethrough and respectively operatively coupled with a corresponding gas outlet for conveying gas from the outlet through and out the passageway. Each of the gas delivery elements is configured for insertion into a respective naris of a patient, and for this purpose the outer wall of the elements are generally frustoconical in shape so as to sealingly engage the naris-defining surfaces of the nose.

Finally, it is very desirable to provide means for selective alteration of the effective position of each of the gas delivery elements individually. This in turn permits custom fitting of the elements with respect to the nares of different patients, so that a single type or size of nasal device can comfortably fit a wide variety of users.

In order to permit alteration of the effective position of the nares elements, the elements may be rotatably mounted to the plenum housing, and moreover may be mounted in appropriate slots permitting selective lateral positioning of the elements with respect to each other. Furthermore, flexible bellows-type corrugated sections can be provided in each of the elements and/or in appropriate positions in the plenum housing, so as to add further ranges of flexibility and adjustability. In order to permit a wide range of angular adjustment of the respective elements, angle shims may be interposed between the bases of the elements and the housing, whereby the elements may be rotated for adjustment purposes. Finally, the elements may be fabricated from relatively soft, deformable, shape-retaining synthetic resin material permitting manual deformation and alteration of the effective shape and position of the elements.

By virtue of the relatively small size of the nasal puff device of the invention, it can be comfortably worn by a patient requiring gas therapy. For this purpose a specialized harness is provided to be worn over the head of the patient which serves to maintain the nasal mask in its operative position.

BRIEF DESCRIPTION OF THE DRAWINGS

FIG. 5 is a perspective view illustrating another embodiment of the invention;

FIG. 6 is a plan view similar to that of FIG. 4 and depicting in phantom certain adjusted positions of the nares elements;

FIG. 7 is an exploded view of one of the nares elements of the embodiments of FIGS. 5 and 6, showing the structure of the nares pillow and the underlying angled shim;

FIG. 8 is a perspective view of a spacer element forming a part of each nares element assembly of the embodiment of FIGS. 5 and 6;

FIG. 9 is a sectional view taken along line 9—9 of FIG. 6 and illustrating the internal construction of the embodiments of FIGS. 5 and 6;

FIG. 10 is a plan view partially in section and with phantom lines illustrating different positions of the nares elements of a third embodiment in accordance with the invention;

FIG. 11 is a sectional view taken along line 11—11 of FIG. 10 and with parts broken away for clarity which further illustrates the construction of the embodiment of FIG. 10;

FIG. 12 is a fragmentary view similar to that of FIG. 10, but illustrating a shifted orientation of one of the legs of the plenum housing;

FIG. 13 is an end view of the embodiment depicted in FIGS. 10-12 with the lefthand nares element shown in bold lines and in phantom to illustrate the range of shiftable movement thereof;

FIG. 14 is an end view from the end of the device opposite that of FIG. 13 and further illustrating in phantom one of the legs of the plenum housing being rotated to different positions;

FIG. 15 is a perspective view of another embodiment in accordance with the invention making use of hollow, deformable nares elements;

FIG. 16 is an exploded sectional view taken along line 16—16 of FIG. 15 to further depict the internal construction of the nasal mask;

FIG. 17 is a vertical sectional view of another embodiment in accordance with the invention which is similar to the embodiments of FIGS. 15-16, but includes filled nares elements having a central gas passageway therethrough; and FIG. 18 is a vertical sectional view of a still further embodiment in accordance with the invention wherein the nares elements include synthetic resin filled, inflatable members.

DESCRIPTION OF THE PREFERRED EMBODIMENTS

Figure 1:
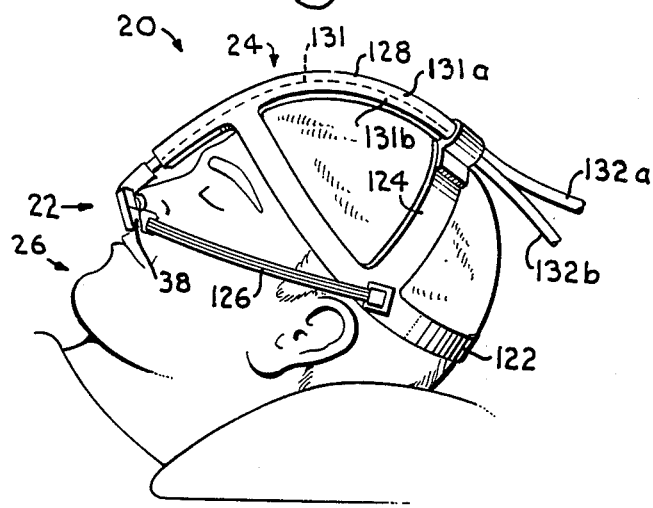
FIG. 1 is a side elevational view of a nasal puff and harness in accordance with the invention, shown operatively mounted on a patient.

Turning now to the drawings, a nasal puff assembly 20 is illustrated in FIG. 1 which broadly includes a nasal puff 22 adapted to be worn adjacent the nose of a patient, together with a harness assembly 24 adapted to be worn over the head of a patient 26. As is readily apparent from a study of FIG. 1, the harness assembly is designed to operatively hold puff 22 adjacent and partially within the nose of the patient 26.

Figure 2:
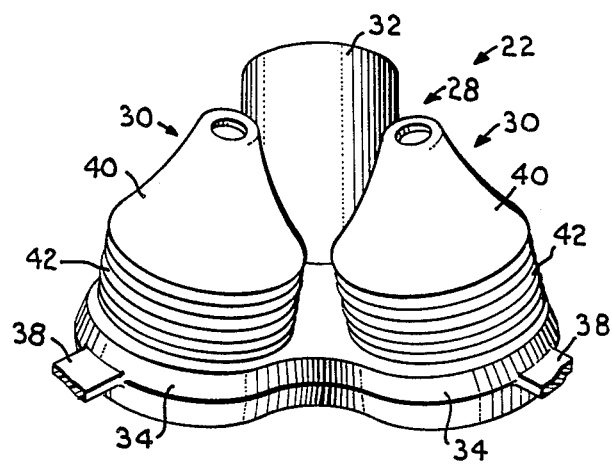
FIG. 2 is a side view of one embodiment of a nasal puff in accordance with the invention, illustrating the plenum housing and nares elements.
Figure 3:
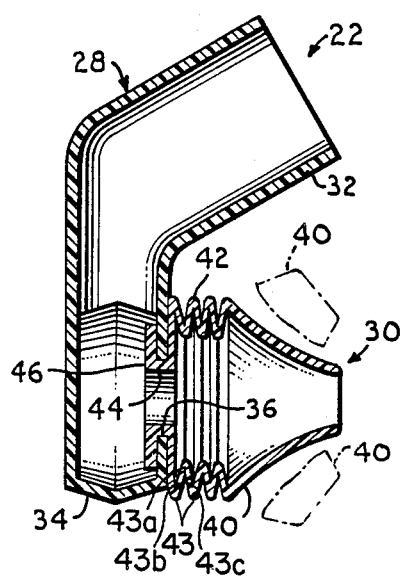
FIG. 3 is a sectional view taken along line 3—3 of FIG. 4.
Figure 4:
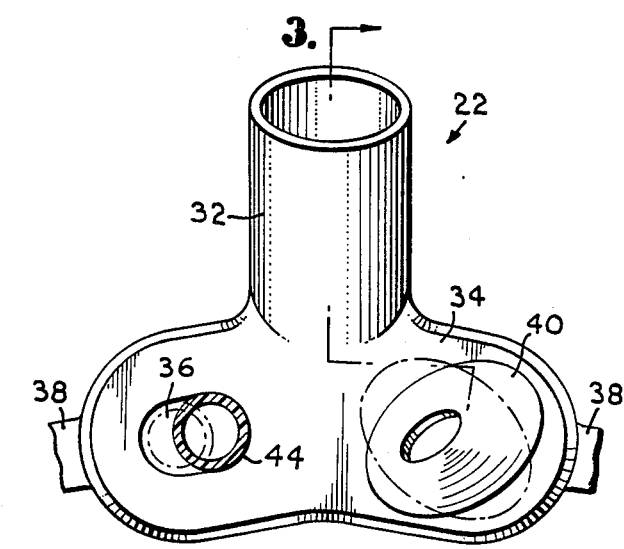
FIG. 4 is a plan view illustrating the structure depicted in FIGS. 2 and 3, with certain altered positions of the respective nares elements being illustrated in phantom.

Referring now to FIGS. 2-4, it will be seen that the puff 22 is in the form of a generally Y-shaped rigid hollow plenum chamber 28 together with a pair of laterally spaced apart nares elements 30. The chamber 28 includes an angularly oriented tubular inlet 32 coupled and communicating with a pair of laterally diverging outlet legs 34. Each outlet leg 34 is provided with an outlet opening in the form of a slot 36 which is generally aligned with the longitudinal axis of the corresponding leg 34. Further, each leg 34 includes an outwardly extending connection clip 38 (shown fragmentarily in FIGS. 2 and 4) permitting connection of the mask to harness assembly 24 as will be described. As best seen in FIG. 3, the chamber 28 is in effect a hollow body with the passageway defined by inlet 32 being in direct communication with the hollow outlet legs 34, and with the respective outlet slots 36.

Each of the elements 30 is of integral construction and includes a somewhat frustoconical but slightly arcuate hollow outermost section 40 leading to and coupled with a bellows-type corrugated section 42. As best seen in FIG. 3, the section 42 presents at least a pair (and preferably a greater number) of axially spaced, circumscribing, outboard peripheral wall segments 43 together with inboard, circumscribing wall segments 43a disposed between and located radially inward of each adjacent pair of outboard wall segments 43. Furthermore, a pair of wall stretches 43b and 43c interconnect each inboard wall segments 43a with both of the assoicated outboard wall segments 43. These stretches 43b and 43c extend generally transverse to the longitudinal axis of the associated gas delivery element, as will be readily apparent from a review of FIG. 3. Finally, a tubular connector section 44 having a radially expanded innermost flange 46 is provided to afford a connection between the element and corresponding outlet leg 34. In particular, and referring specifically to FIG. 3, it will be observed that the element 30 is mounted to an associated leg 34 with the tubular connection section 44 being received within the slot 36 and with flange 46 serving to sealingly maintain the element in covering relationship to the slot 36.

From the foregoing description of the structure of puff 22, it will be readily appreciated that the unit can be easily altered to fit a variety of patients. Thus, the elements 30 can be rotated as illustrated in phantom in FIG. 4 and moreover can be shifted laterally within the outlet slots 36 as depicted in the lefthand leg of FIG. 4. Finally, it will be appreciated that the corrugated sections 42 permit the elements to be manually deformed so as to assume the most advantageous angular position for a particular patient. Exemplary element positions making use of this feature are shown in phantom in FIG. 3.

Attention is next directed to FIGS. 5-9 which illustrate another nasal puff 48 in accordance with the invention. In this instance, the mask includes a somewhat Y-shaped in plan hollow plenum chamber 50 having a tubular inlet 52 and a pair of hollow diverging outlet legs 54, each of the latter having an outlet recess 56 therein.

In the case of puff 48, each of the nasal elements is in the form of an assembly including a hollow rotatable body 58, hollow angle shim 60 and finally hollow frustoconical naris pillow 62. In particular, the body 58 (see FIG. 8) is formed of rigid synthetic resin material and includes a gas inlet 64 and an offset gas outlet 66. Each body 58 is designed to fit within the associated outlet recess 56, and for this purpose the recess 56 includes a specially configured lower shelf 68 having an opening 70 therethrough. As illustrated in FIGS. 8 and 9, the lowermost end of each body 58 is in the form of a tubular extension having a radially expanded connection rim 72 permitting an axially rotatable retention of the body within opening 70.

The angle shim 60 includes an upstanding tubular wall 74 which terminates in an angularly disposed, radially enlarged flange portion 76. The central opening defined by the shim 60 is coaxially aligned with outlet opening 66 of the body 58. A rotatable connection is provided between the shim 60 and the upper tubular portion of body 58 defining opening 66, by means of a recess 78 provided in the internal face of wall 74 receiving the upper tubular portion of the body 58.

Finally, a naris pillow 62 is secured to flange portion 76 by adhesion or any convenient means. As in the above described embodiment, the pillow 62 is formed of soft synthetic resin material so as to comfortably fit within a naris of a patient. For example, the pillow may be formed of open or closed cell foam (skinned or unskinned), gel filled skinned materials, or the silicones. Of course, the material in actual contact with the patient's skin should be biocompatible. The general shape of the pillow 62 is frustoconical in cross section, with a slight arc in the sidewall thereof. As is evident from a study of FIGS. 5–9, each pillow 62 has a central air passageway 80 therethrough.

In the use of puff 48, the respective pillows 62 can be shifted through the expedient of rotation of the underlying angle shims 60, and in this manner a wide angular orientation of the individual pillows can be achieved. Further, the individual pivotal bodies 58 can be rotated as desired to provide a further range of positions for the nares elements. Thus, FIG. 6 illustrates the righthand nares element in two possible positions thereof, effected through use of the adjustable components of the element as described.

FIGS. 10–14 illustrate another nasal puff 82. In this instance the mask 82 is provided with a hollow bifurcated plenum chamber 84 and a pair of nares elements 86 respectively coupled with the legs of chamber 84. In more detail, it will be observed that the chamber 84 includes a tubular inlet 88 which is obliquely oriented as best seen in FIG. 11 together with a pair of separate tubular outlet legs 90 extending from and being in communication with inlet 88. Each of the legs 90 includes a tubular connection portion 92 together with a laterally extending terminus provided with an elongated outlet slot 94 therein. A bellows-type corrugated section 96 serves to interconnect each connection portion 92 and the associated laterally extending leg section, so as to provide a means of altering the position of each outlet leg with respect to the other.

The elements 86 are in the form of elongated, outwardly projecting members terminating in hollow, frustoconical, soft synthetic resin nares pillows 98. Connection between the pillows 98 and the associated legs 90 is afforded by means of a flexible, corrugated, bellows-type connection shank 100 which is slotted and presents an innermost connection flange 102. The flange 102 serves to rotatably mount each element 86 within a slot 94, with the overall size of the shank 100 serving to seal the slot regardless of the position of the element. Further, the bellows shanks 100 also provide degrees of additional adjustability.

In the case of mask 82, the effective position of the elements 86 can be altered by rotation of the elements and/or deformation of the bellows shanks 100; shifting thereof within their associated slots 94; and/or deformation of the legs 90 with respect to the connection portions 92 through use of the corrugated sections 96. Various possible positions of the nares elements achieved through one or more of the aforementioned features are illustrated in phantom in FIGS. 10 and 12–14.

FIGS. 15 and 16 illustrate a simplified nasal puff 104 including a Y-shaped hollow plenum chamber 106 and a pair of soft, deformable hollow nares elements 108. As seen in FIG. 16, the elements 108 are essentially integrally formed with the forward face 110 of chamber 106, but by virtue of the soft, deformable synthetic resin material used to fabricate the elements 108, they can be readily deformed by the user to give a comfortable fit. As in the case of the other embodiments described previously, chamber 106 includes an inlet 112 which communicates with the outlet openings 114 in the respective nares elements.

FIG. 17 illustrates an embodiment 104a in accordance with the invention. In this embodiment a plenum chamber 106a is provided in the form of a hollow body leading to a pair of laterally spaced apart openings 115. The chamber 106a includes an inlet 112a, and in this embodiment it will be seen that an air delivery hose 116 is coupled with inlet 112a. Nares elements 108a form a part of mask 104a and are similar in most respects to the hollow elements 108 previously described. In this instance though, an inner fill 118 is provided of gel or other soft deformable material, with the inner fill defining a central air passageway 120 communicating with the outlet openings 114a. Here again, alteration of the effective position of the nares elements 108a in the embodiment of FIG. 17 is effected by manual deformation of these elements as required.

Attention is next directed to FIG. 18 which depicts a final embodiment 104b. In this embodiment a plenum chamber 106b is provided in the form of a hollow body leading to a pair of laterally spaced apart, upwardly and obliquely extending tubular sections 115'. The chamber 106b includes an inlet 112b with an air delivery hose 116b coupled with the inlet 112b. In this embodiment nares elements 108b are each in the form of hollow, somewhat egg-shaped, soft, expandable synthetic resin outer membranes 109b which surround the respective tubular sections 115'. A quantity of synthetic resin foam fill 118b is received within each membrane 109b in surrounding relationship to the corresponding inner tubular section 115'. In addition, an elongated, relatively thin, tubular inflation/deflation tube 119 is operatively coupled to the interior of each of the foam-filled inner spaces defined by the membranes 109b and associated tubular sections 115'. The outer end of each tube 119 (not shown) is provided with a fitting permitting application of air via a syringe or other expedient into the tube, and alternately pulling of a vacuum therethrough. In the use of the embodiment of FIG. 18, a vacuum may be drawn through each of the respective tubes 119 in order to constrict the nares elements 108b to a relatively small size. At this point the nares elements can be inserted into the nasal passages of a patient whereupon positive pressure air is fed through the tubes 119 in order to inflate the membranes 109b into a comfortable comforming relationship to the nares passages of the patient. Application of medicinal gas can then proceed in the usual fashion. In this connection, the nasal puff assembly of this embodiment is in some respects similar to the structure described in U.S. Pat. No. 3,640,282, which is incorporated by reference herein.

The preferred harness assembly 24 (see FIG. 1) of the invention is adapted to be worn on the head of patient 26 and includes a main harness strap 122 and a cross strap 124. A pair of flexible mask-retaining straps 126 are respectively secured to main strap 122 as shown, and extend to a point for connection with the clips 38 provided on sides of the nasal puff (such clips have not been fully depicted on all of the embodiments described, but it will be understood that these clips or their equivalent, e.g., Velcro strips, are generally provided in order to maintain the nasal masks in place).

In addition, the harness assembly 24 includes an elongated gas-conveying tube 128 which is adapted for coupling with the inlet of the nasal puff and extends upwardly along the length of the bridge of the patient's nose and across the patient's forehead, terminating at the top of the patient's head as at 130. It will be observed in this respect that the tube 128 is longitudinally bifurcated by means of an elongated, central wall 131 serving to divide the overall tube 128 and present a pair of elongated, juxtaposed passageways 131a and 131b. The upper end of the tube 128 is provided with a Y-shaped fitting leading to a pair of elongated tubes 132a, 132b. One of the tubes 132a leads to a source of pressurized air (not shown), whereas tube 132b is an exhaust or discharge tube. Use of such a dual or bifurcated tube arrangement provides a means for purging patient-generated $CO_2$ during exhalation.

It will thus be seen that the present invention provides a greatly improved nasal puff assembly which can be comfortably worn during a period of sleep by patients suffering from obstructive sleep apnea. Use of nares elements of the type described permits an effective sealing engagement between the elements and the defining surfaces of the patient's nares, so as to permit appropriate gas therapy without undue leakage. At the same time, the adjustability of the elements means that only a relatively small number of sizes of masks need be manufactured and stocked, inasmuch as a given mask may be modified to fit a variety of patients. Also, since the sealing surfaces around a patient's nares are smaller than the area around the entire nose, less force is required with the nasal puffs of the invention to achieve a sealing fit than in the case of conventional nose masks which seal around the nose. Thus, the mounting straps need not be pulled as tightly with the puff devices hereof, giving a more comfortable fit to the patient.

It will also be appreciated that while the present invention has been described chiefly in connection with the treatment of sleep apnea, the improved nasal puff assemblies hereof may also be used for other gas therapies.

We claim:

1. A nasal puff, comprising:
   a plenum chamber including structure defining an inlet adapted for coupling with a source of gas, and a pair of separate, spaced apart gas outlets in communication with said inlet; and
   a pair of elongated gas delivery elements each having a structure defining gas flow passageway therethrough and respectively operatively coupled with a corresponding gas outlet for conveying gas from the outlet through and out said passageway,
   said elements each being configured to present an end portion for insertion into a respective naris of a patient to receive said gas,
   there being means for selective alteration of the effective position of each of said elements individually for permitting custom fitting of said elements with respect to the nares of different patients,
   said gas delivery element alteration means including, for each element, an elongated bellows-type corrugated section forming a part of said passageway-defining structure and located between the corresponding end portion and said plenum chamber,
   each of said corrugated sections including at least a pair of axially spaced apart outboard peripheral wall segments, an inboard wall segment disposed between and located radially inward of the outboard wall segments, and a pair of wall stretches interconnecting said inboard wall segment and both of said outboard segments, said wall stretches extending generally transverse to the longitudinal axis of the associated gas delivery element.

2. The nasal puff of claim 1, said plenum chamber being a generally Y-shaped hollow body, with said outlets being located in the branches of said body.

3. The nasal puff of claim 2, said body being substantially rigid.

4. The nasal puff of claim 1, each of said end portions of said elements presenting an elongated, generally frustoconical outer wall for sealingly engaging the defining surfaces of a patient's naris.

5. The nasal puff of claim 1, each of said outlets comprising an elongated slot, each corresponding element including a tubular member received by and slidable within the associated slot, whereby each of said elements may be bodily shifted to effect an alteration in the effective position thereof.

6. The nasal puff of claim 1, each of said elements being rotatable relative to said chamber.

7. The nasal puff of claim 6, including an angle shim interposed between each of said elements and the corresponding housing outlet.

8. The nasal puff of claim 1, each of said elements being formed of a deformable, shape-retaining soft synthetic resin material permitting manual alteration of the effective shape and effective position of each of said elements.

9. The nasal puff of claim 1, said inlet comprising an elongated tubular section adapted for connection to a flexible hose coupled with said gas source.

10. The nasal puff of claim 1, including means for securing said mask in its operative disposition adjacent a patient's nose with said element end portions inserted into the nares of a patient.

11. A nasal puff, comprising:
   a plenum chamber including structure defining an inlet adapted for coupling with a source of gas, and a pair of separate, spaced apart gas outlets in communication with said inlet; and
   a pair of gas delivery elements each having a gas flow passageway therethrough and respectively operatively coupled with a corresponding gas outlet for conveying gas from the outlet through and out said passageway,
   said elements each being configured for insertion into a respective naris of a patient to receive said gas,
   there being means for selective alteration of the effective position of each of said elements individually for permitting custom fitting of said elements with respect to the nares of different patients,
   each of said outlets comprising an elongated slot, each corresponding element including a tubular member received by and slidable within the associated slot, whereby each of said elements may be bodily shifted to effect an alteration in the effective position thereof.

12. A nasal puff, comprising:
   a plenum chamber including structure defining an inlet adapted for coupling with a source of gas, and a pair of separate, spaced apart gas outlets in communication with said inlet; and
   a pair of gas delivery elements each having a gas flow passageway therethrough and respectively operatively coupled with a corresponding gas outlet for conveying gas from the outlet through and out said passageway, said elements each being configured for insertion into a respective naris of a patient to receive said gas, there being means for selective alteration of the effective position of each of said elements individually for permitting custom fitting of said elements with respect to the nares of different patients, each of said elements being rotatable relative to said chamber, there being an angle shim interposed between each of said elements and the corresponding housing outlet.

* * * * *